United States Patent [19]

Chin et al.

[11] 4,332,159
[45] Jun. 1, 1982

[54] REID VAPOR PRESSURE TESTER

[75] Inventors: Thomas G. Chin; Arthur Alston, both of El Cerrito, Calif.

[73] Assignee: Chevron Research Company, San Francisco, Calif.

[21] Appl. No.: 182,365

[22] Filed: Aug. 29, 1980

[51] Int. Cl.³ .......................................... G01N 7/16
[52] U.S. Cl. .................................................. 73/64.2
[58] Field of Search ............................... 73/64.2, 29

[56] References Cited

U.S. PATENT DOCUMENTS

| | | | |
|---|---|---|---|
| 2,540,377 | 2/1951 | Pachaly | 73/64.2 |
| 2,671,341 | 3/1954 | Jacobs | 73/64.2 |
| 2,764,017 | 9/1956 | Ronnebeak | 73/64.2 |
| 2,811,851 | 11/1957 | Jacobs | 73/64.2 |

Primary Examiner—S. Clement Swisher
Attorney, Agent, or Firm—G. W. Wasson; J. A. Buchanan, Jr.

[57] ABSTRACT

A method and apparatus for measuring Reid Vapor Pressure, as defined in ASTM D-323 procedure, of liquid hydrocarbon materials including a totally contained system having a sample preparation portion and a measurement portion. The method and apparatus is totally automated in preparing the apparatus for measurement and in performing the measurement.

20 Claims, 2 Drawing Figures

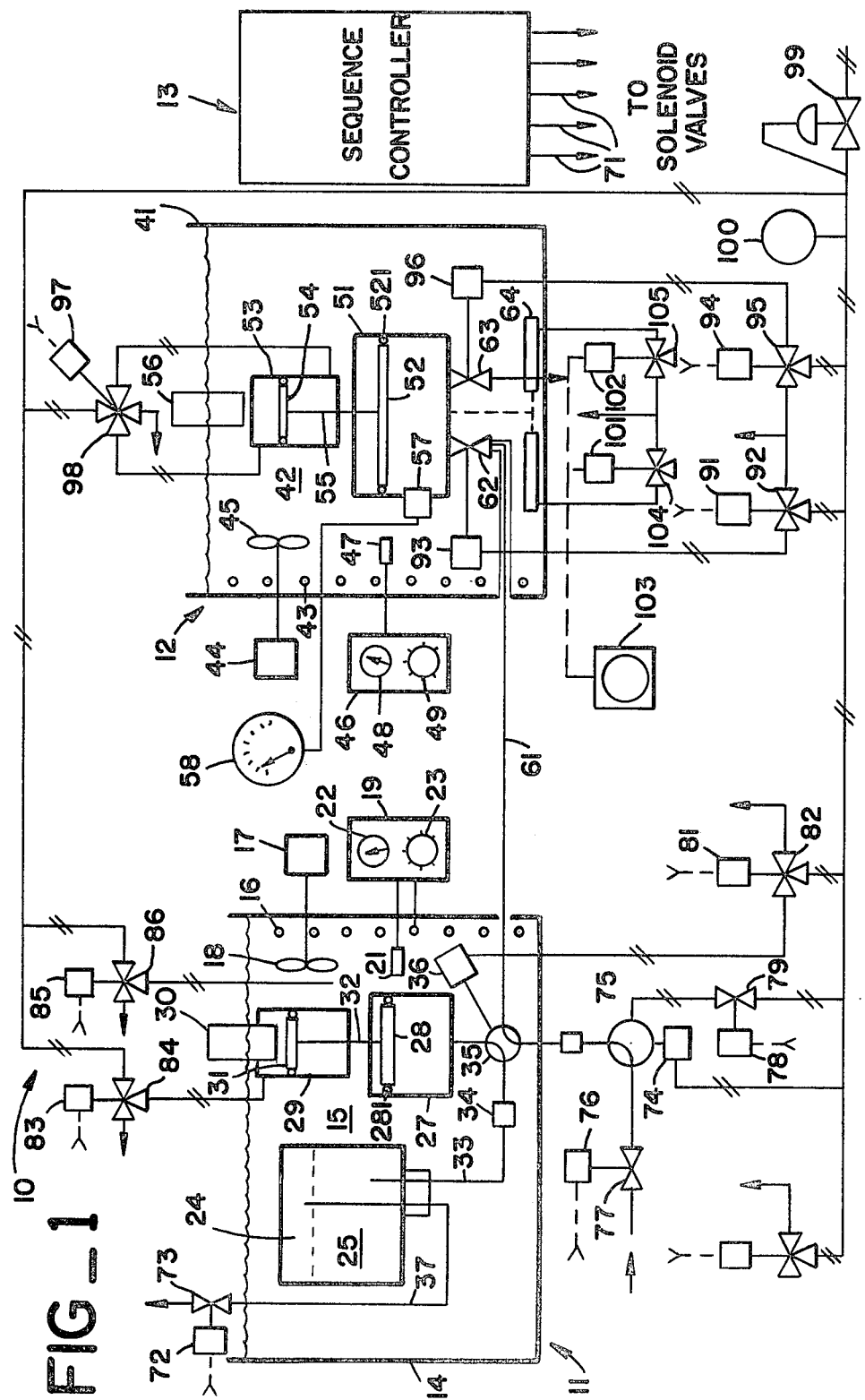

| OPERATION | TIME MIN. SEC. | TYP. CAN AIR VALVE 73 | 4-WAY VALVE 35 | PURGE AIR VALVE 79 | WATER VALVE 77 | 3-WAY VALVE 75 | SAMPLE CYLINDER PISTON 28 | MEASURING CYLINDER INLET VALVE 62 | MEASURING CYLINDER DRAIN VALVE 63 | MEASURING CYLINDER PISTON 52 | SHAKER 64 |
|---|---|---|---|---|---|---|---|---|---|---|---|
| FIG-1 ITEM NO. | | | | | | | | | | | |
| FILL SAMPLE CYLINDER | 0 6<br>0 9 | | | | | | | | | | |
| FLUSH THROUGH MEASURING CYLINDER | 1 1<br>0 28 | OPEN | ⊘ | | | | UP | | | | |
| REPEAT FLUSH | 0 34<br>0 36<br>0 51<br>0 58 | OPEN | ⊘ | | | | UP | | | | |
| START AIR PURGE | 2 23<br>2 37 | | | OPEN | | | | | | | |
| FILL SAMPLE CYLINDER | 2 38<br>2 55 | OPEN | ⊘ | | | | UP | | | | |
| END AIR PURGE | 3 0<br>3 9 | | | | | | | | | | |
| WATER FLUSH | 3 20<br>3 23 | | | | OPEN | W⊘A | | | | | |
| SHAKE & DRAIN | 3 30<br>3 39 | | | | | | | | | | |
| AIR PURGE | 4 3<br>4 12 | | | OPEN | | | | | | | |
| SHAKE (TEMP. EQUILIBRIUM) | | | | | | | | | | | ON |
| SAMPLE INTO MEASURING CYLINDER | 5 29 | | | | | | | | CLOSED | | |
| CLOSE MEASURING CYLINDER | 5 50 | | | | | | | CLOSED | | | |
| EXPAND TO 5 VOL | | | | | | | | | CLOSED | DOWN | |
| SHAKE FOR EQUILIBRIUM | | | | | | | | | | | ON |
| NOTE RVP | | | | | | | | | | | ON |
| DRAIN | | | | | | | | | | | |

FIG-2

REID VAPOR PRESSURE TESTER

BACKGROUND OF THE INVENTION

The present invention relates to an apparatus for determining the vapor pressure of a fluid. The apparatus is especially useful in the direct determination of Reid Vapor Pressure (hereinafter sometimes referred to as RVP) of a volatile petroleum product. The invention more particularly is directed to an apparatus and method for producing accurate and reproducible RVP measurements of volatile, normally liquid, hydrocarbon fuels.

Automotive gasoline is a product which is manufactured in large quantities by petroleum refiners to a set of refiner's specifications. Automotive gasolines also must comply with certain set specifications which are established by various State regulations which include limited variations for geographic locations and seasonal changes. The specifications for automotive gasoline are established in American Society for Testing Materials (ASTM) specifications designated D-439. These specifications establish the required properties of automotive gasolines for ground vehicles, and they describe various characteristics of automotive gasolines which may be used in a wide range of operating conditions. The specifications allow automatic variation to the gasoline manufacturer to meet the requirements of seasonal changes in temperature, depending upon the locality in which the product is to be used. This is done by providing five volatility classes and differentiating the use of the volatility classes according to the months of the year and the geographical location in the United States where the product is expected to be used.

The ASTM specification D-439 establishes a schedule of changes within the volatility classes for seasonal and geographical differences. From the D-439 specification a gasoline manufacturer may determine the volatility characteristics of the gasoline that may be produced and sold in any particular geographic location at a particular season of the year. Reid Vapor Pressure is one of the volatility measurements established in the D-439 specification for automotive gasoline.

In the manufacture of motor gasolines, the manufacturer blends into the product a number of different hydrocarbon materials. The end product that is produced from the blending operation must conform to the D-439 specifications for an automotive gasoline. The specifications may include anti-knock performance, vapor-liquid ratio, Reid Vapor Pressure, a distillation characteristic, corrosion, existent gum, sulfur, and other specific requirements for the respective geographic locations.

Reid Vapor Pressure of motor gasoline is measured by another separate ASTM standard D-323 which prescribes how a sample of motor fuel is to be handled and establishes the absolute procedure that must be used in determining Reid Vapor Pressure using a specific air chamber referred to as a vapor tester bomb. RVP measurements in accord with the D-323 procedure take a substantial period of time (about 25 minutes, plus equipment preparation time) and the measurements are subject to variations due to variations in sample handling, test conditions, and equipment preparation all of which lead to imprecise test results. Such delay and imprecision in the measurement of RVP by the D-323 apparatus is incompatible with the continuous process of producing blended motor fuels in the manufacturing of gasoline products.

It is therefore believed to be advantageous to develop a substantially completely automated procedure for handling motor gasoline samples and for measuring the RVP of these samples. Preferably, the procedure can be accomplished with a self-contained measurement device that will produce a direct measurement of the actual RVP of the product being produced. With such a procedure and device a motor fuel manufacturer may have a quick and precise indication of the RVP of the product being produced in a motor gasoline blending operation.

There is but one way to measure RVP directly and that is to use D-323. The present invention duplicates the essential conditions of D-323; thus it is designed to measure RVP directly without the need for corrections. Previous automated devices of which we are aware do not duplicate D-323, therefore their results must be correlated with RVP. A measurement which must be correlated with RVP includes a correlation error and the resultant measurement is therefore likely to be less accurate than a direct measurement.

The following specification describes an apparatus, and a method for operating the apparatus, for providing a rapid, accurate, reproducible and dependable measurement of Reid Vapor Pressure—RVP.

SUMMARY OF THE INVENTION

The present invention provides an improved apparatus for directly determining the RVP of a volatile crude oil product in accordance with the standards established in ASTM D-323 entitled "Standard Test Method for Vapor Pressure of Petroleum Products (Reid Method)".

In accordance with the present invention, a self-contained RVP measuring device is provided which includes a sample container conforming to the standards of the ASTM D-323 test. The sample container is adapted to be immersed in a liquid bath at the prescribed D-323 temperature. Valving, conduits and control mechanisms are associated with the sample container permitting a metered quantity of the sample material to be extracted from the sample container. The invention further includes a measuring cylinder to which the metered quantity of the sample material may be passed for the direct measurement of RVP. The measuring cylinder is maintained in a liquid bath and shaken in accordance with the requirements of the D-323 test.

The apparatus of the present invention is further provided with automated and controlled valves which control the purging of interconnecting conduits as well as the sample cylinder and measuring cylinder in accordance with the D-323 test to place the apparatus in condition for making accurate RVP measurements and for purging the system between measurements. When operated in accordance with the procedures herein described, the apparatus of the present invention provides for the direct measurement of RVP of volatile hydrocarbon products in accord with ASTM D-323.

BRIEF DESCRIPTION OF THE DRAWINGS

FIG. 1 is a schematic drawing illustrating the apparatus of the present invention including the sample conditioning and RVP measurement cylinders and the control mechanisms adapted to transport samples from sample storage to the sample measurement elements.

FIG. 2 is a chart relating operations, time and control mechanism condition for elements of FIG. 1.

DESCRIPTION OF THE PREFERRED EMBODIMENT

The elements of the preferred embodiment of the apparatus herein disclosed are intended to function in accordance with the procedure required by ASTM D-323. In the apparatus shown a sample cylinder is filled with a chilled sample of the volatile hydrocarbon product, then the chilled sample is transported to an air chamber immersed in a constant temperature bath at 100° F. and shaken until vapor/liquid equilibrium is reached within the chamber. The pressure reading corresponding to the pressure within the air chamber is the Reid Vapor Pressure—RVP for the product. The sample itself must be prepared in accordance with the precise requirements of the ASTM D-323 test and, for the measurement to be an accurate measurement, all conducting tubes between the sample cylinder and the measuring cylinder must be properly purged with water and instrument air to be sure that, before each measurement, any trace of volatile hydrocarbon samples from a previous measurement are removed. All of the foregoing requirements are satisfied with the apparatus of the present invention.

The RVP measuring apparatus as illustrated constitutes an assembly 10 having a sample preparation portion 11, a sample measuring portion 12, a sequence controller 13 and the necessary air, water and control valve system therefor attached to the sample preparation and sample measuring portion under the control of the controller 13.

The sample preparation portion 11 constitutes a cold sample holder 14 for containing a liquid bath 15, including means 16 for cooling the liquid and a stirring mechanism 17 for driving a blade member 18 within the container for circulating the fluid over the cooling means 16. A temperature sensor and controller 19, outside of the container, includes means connecting the sensor to an internal temperature sensing element 21 and means to control the operation of the cooling means 16. The temperature sensor and controller includes a means 22 for registering the temperature of the fluids within the holder 14 and suitable means 23 for adjusting the operation of the cooling means 16. An alternate and simpler form of cooling system would be the use of ice melting in a water bath to maintain the bath at about 32° F.

Inside the holder 14 is a sample container 24, supported on means not shown, for holding samples of the hydrocarbon whose RVP is to be measured in a manner consistent with the provisions of ASTM testing procedures D-323. The support of the sample container within the holder 14 permits the container to be held either in an upright or an inverted position, as illustrated in the drawing, so that a portion of the sample of hydrocarbon 25 within the container may be withdrawn from the bottom of the container in a gravity flow.

Immersed in the fluid within the cold sample holder 14 is a sample cylinder 27 having an internal plunger 28 with a seal 281 operating against the interior of the cylinder 27 and operated by an air actuator 29 including an adjustable upper stop 30 and a plunger 31 connected by rod 32 to the internal plunger 28 within the sample cylinder 27. The sample container 24 is connected to the sample cylinder 27 by suitable piping 33. Included in the piping line is a one-way valve 34 and a four-way ball valve 35 having an actuator 36. Piping 37 supplies air to the sample container 24.

The sample measuring portion 12 includes a hot sample holder 41 containing a fluid 42. A means 43 is provided for heating the fluid 42 to a desired temperature and an external stirrer 44 having an internal blade 45 is provided for circulating the fluid. A temperature controller 46 includes a temperature sensor 47 with a temperature gauge 48 on the controller and a temperature adjuster 49 to set the desired fluid control valve (100° F.). Inside the hot sample holder 41 immersed in the heated fluid 42 is a measuring cylinder 51 having an internal plunger 52 with a seal 521 operating against the interior of the cylinder 51 and operated by an air actuator 53 including an internal plunger 54 connected by rod 55 to the plunger 52. An adjustable upper stop 56 is mounted above the air actuator 53 to provide a control for the movement of the air actuator and its control of the movement of plunger 52.

A pressure sensing gauge 57 is mounted in the wall of the sample measuring cylinder 51 and connected by suitable means to a pressure registering meter 58 outside of the hot sample holder 41.

The hot sample holder 41 and the measuring cylinder 51 are connected to the cold sample holder 14 and the sample cylinder 27 through the four-way valve 35 and through piping 61 passing into the hot sample holder 41 and, through suitable valving 62 at the bottom, to the sample measuring cylinder. A second set of valving 63 is connected to the bottom of the measuring cylinder 51 to provide a drain for samples and washes brought into the measuring cylinder. A suitable shaker mechanism 64 is mounted within the hot sample holder 41 including mechanical means connecting it to the measuring cylinder 51 to shake the measuring cylinder in accordance with the requirements of ASTM standard D-323.

The sequence controller 13 includes conventional mechanisms for operating the plurality of solenoid valves associated with the control mechanisms in the desired sequence of operation. As illustrated in the drawing a plurality of output signals are provided at 71 with arrows intended to indicate that the output is connected to individual solenoid operators or actuators.

In the form of the apparatus illustrated in the drawing, the RVP measuring device is provided with supply water for flushing and supply air for operating and purging the various valves and plungers of the system. Solenoid operator 72 operates valve 73 in supplying input and venting air to the sample storage container 24 through piping 37. Solenoid 74 operates valve 75 in supplying either air or water to the elements in the cold sample holder 14 and the hot sample holder 41. Solenoid 76 operates valve 77 to supply flushing water to valve 75 and solenoid operator 78 operates valve 79 to supply air to the valve 75. Solenoid 81 operates valve 82, a three-way valve, to supply operating air to actuator 36 for four-way ball valve 35. Solenoid 83 operates a three-way valve 84 and solenoid 85 operates valve 86 to control the supply of operating air to one side or the other of plunger 31 in actuator 29 to move plunger 28 to draw a sample from the sample container 24 into the sample cylinder 27 or to move the sample to the measuring cylinder 51.

Associated with the hot sample holder are the following solenoids and valves. Solenoid 91 operates valve 92 to supply operating air to actuator 93 for the operation of valve 62 and solenoid 94 operates valve 95 to provide operating air to actuator 96 for the operation of valve 63. Operation of the valves 62 and 63 are provided for the supply and withdrawal of samples into or from the measuring cylinder. Solenoid 97 operates four-way valve 98 to supply air to either side of air actuator 53 to cause plunger 54 to move up or down to drive plunger 52 in the measuring cylinder. A pressure reducing valve 99 controls the air pressure to the operators for all of the valves and a gauge 100 is supplied to indicate the regulated air pressure. The pair of solenoids 101 and 102 are supplied through a delay relay 103 to operate valves 104 and 105, respectively, to supply vibrational power to the shaker 64 within the hot sample holder 41. An alternative shaker system may include a motor driven mechanism for producing a desired vibration.

In accord with the RVP test method D-323, the sample container holding the liquid hydrocarbon must have liquid content between 70% and 80%. The container is examined, shaken vigorously, sealed and returned to a cooling bath where it is completely immersed for adequate time to allow container and sample to reach the bath temperature of 32° F. to 40° F.

The measuring cylinder is purged and rinsed and then immersed in the heated bath until it has reached the bath temperatures of 100° F.±0.2° F. The measuring cylinder 51 is first water rinsed and air purged to assure that any previous sample is removed and to provide water to saturate the cylinder of air. Test procedures will establish steps which will assure that the measuring cylinder and connecting piping are adequately rinsed and purged.

In the apparatus of FIG. 1, sample container 24 is prepared and filled in accord with D-323 test procedures. When properly filled, the container is inserted and immersed in the bath within cold sample holder 14 with air supplied through valve 73 and piping 37. The sample container is connected through piping 33, one way valve 34 and four-way valve 35 to sample cylinder 27.

Sample cylinder 27 is empty prior to a sample collection with internal plunger 28 down at the bottom of cylinder 27. Under control of sequence controller 13, plunger 28 is raised by actuator 29 by moving plunger 31 to its upper limit against adjustable upper stop 30. Valve 35 is open to permit a sample to be drawn into the cylinder 27 and valve 73 to open to permit air to pass into sample container 24 through piping 37.

After a suitable time interval, the sequence controller 13 changes valve actuation and the plunger 28 is lowered to push the sample from cylinder 27 through valve 35, piping 61 and valve 62 into measuring cylinder 51. Under control of sequence controller 13, the sample is either passed out through drain valve 63 or into the measuring cylinder 51 when plunger 52 is raised by operation of actuator 53 raising its plunger 54.

Measuring cylinder 51 must be properly prepared according to D-323 standards prior to its use as the measuring cylinder for measuring RVP. To accomplish that preparation the apparatus of the present invention and its sequence of operations provides for an air purge followed by a water wash of the cylinder and its connecting piping and an air purge of the cylinder and the piping after the water wash and before measurement on a sample. The sequence of these operations is shown in chart form in FIG. 2.

Sequence controller 13 operates four-way valve 35 to its normal position as shown in FIG. 1 and places three-way valve 75 and valve 79 in position to pass air through valves 79, 75, 35, piping 61, valve 62 and into measuring cylinder 51. In the typical time sequence, as shown in FIG. 2, the air purge begins at about 2 minutes, 8 seconds with air purge valve 79 open until about 3 minutes, 20 seconds. During that interval the measuring cylinder piston 52 is raised and the interior of the measuring cylinder and the piping lines are air purged until the air valve 79 is closed.

At about 3 minutes and 30 seconds, the water valve 77 is opened while the four-way valve 35 remains in the same setting and water is passed into the measuring cylinder. The wash water flows through the valves, piping and measuring cylinder 51 and out through drain valve 63. At about 3 minutes and 39 seconds, the drain valve 63 is closed, the measuring cylinder is water washed and shaker 64 is energized to shake the measuring cylinder for a short interval. At about 4 minutes and 3 seconds drain valve is again opened and the piston 52 of measuring cylinder 51 is moved downward to force water out through drain valve 63. At about 4 minutes and 12 seconds the water valve 77 is closed and the water wash is terminated and, at the same time valve 75 is operated to disconnect the water system for the measuring apparatus and its piping. For a short interval air valve 79 is opened to air purge the piping and the measuring cylinder. After the purge air has been cut off, the measuring cylinder with the inlet valve 62 and the drain valve 63 open, is shaken to accelerate the temperature equilibrium of the contained air.

At about 5 minutes 29 seconds the drain valve 63 is closed and soon thereafter four-way valve 35 is returned to the position shown in FIG. 1 to connect the sample cylinder 27 to the measuring cylinder 51. At about 5 minutes and 50 seconds sample cylinder piston 28 is conditioned to be lowered to pass the metered sample from sample cylinder 27 to the measuring cylinder. Soon thereafter, inlet valve 62 is closed and measuring cylinder piston 52 is raised to expand the measuring cylinder volume by ¼ (the volume of the liquid present in the cylinder). This expansion increases the volume of the measuring cylinder from 4 times to 5 times the sample volume and thus simulates the condition which prevails in the ASTM D-323 test after the filled sample cylinder is coupled to the air chamber. After this expansion, the measuring cylinder is shaken to establish (1) vapor-liquid equilibrium between the two phases in the cylinder and (2) thermal equilibrium throughout the cylinder, its contents and the surrounding 100° F. bath. After these equilibria are established, the pressure within the measuring cylinder (the RVP of the sample) is sensed by sensor 57 and observed at meter 58.

When an RVP has been determined, the measuring cylinder inlet valve 62 and the drain valve 63 are opened and the apparatus is ready to start reading RVP of another sample. Between each sample RVP reading, the cylinders, piping and valves are air-purged, water washed and air purged again to assure that the apparatus is properly prepared according to D-323.

The RVP test of the present invention has built-in capabilities for a number of tests, i.e. leakage in the cylinders and connecting tubing, air/liquid volume ratio in measuring cylinder and correct sample cylinder (liquid) volume. The following describes how these tests are accomplished.

Leakage

This is tested with the bath filled and temperature controlled to 100° F.±0.2° F. Introduce enough air into the measuring cylinder 51 to give a transducer readout at the gauge 58 of say 10 psig. (drain valve 63 closed). Lock in the air by closing the inlet valve 62. Allow a few minutes for the air to reach the bath temperature. The pressure at the gauge 58 should hold steady to ±0.01 psi for more than 15 minutes. Repeat the test for the other position of piston. Since the measuring cylinder 51 is now known to be leak tight, the inlet valve 62 can be opened and the test can be extended to the tubing 61 and, by operating the four-way valve 35, to the sample cylinder 27 with piston 28 up and down.

Measuring Cylinder Air/Liquid Volume Ratio

D-323 requires an air/liquid volume ratio of 4 to 1, ±0.2. Thus the measuring cylinder must have 4 times the sample volume with its piston down and 5 times the sample volume with its piston up. These volumes can be checked by introducing dry air into a dry cylinder 51 with piston 54 down (volume $V_1$) to attain a pressure of about 10 psig. Inlet valve 62 is closed and the pressure is allowed to stabilize (gauge pressure $P_1$). Piston 54 is then raised to the "up" position (volume $V_2$) and the pressure is again allowed to stabilize (gauge pressure $P_2$). P2 should equal ($P_1$+barometric press)×4/5—barometric pressure since $V_2$ should be $5/4 \times V_1$, for isothermal expansion of a perfect gas. The measuring cylinder stop is adjusted to correct this volume ratio as necessary. This ratio $V_1/V_2$ may be further adjusted slightly to account for the small volume of air in the tubing between the cylinders which is pushed into the measuring cylinder ahead of the liquid sample.

Liquid Volume—Sample Cylinder Adjustment

Now the sample cylinder volume can be adjusted to equal the volume swept by the measuring cylinder piston 54 ($V_2-V_1$). With both cylinders clean and dry and at ambient temperature, sample cylinder piston 28 up, measuring cylinder piston 52 down, close the measuring cylinder drain valve 62. Note the transducer gauge reading (zero reading). Operate the sample cylinder piston 28 down and wait for pressure gauge readout to stabilize. Close the measuring cylinder inlet valve 62 and raise the measuring cylinder piston 52. Pressure at the gauge should return to zero reading. Adjust sample cylinder piston stop as necessary and repeat.

This automatically accounts for the liquid remaining in the tubing at the end of the sample cylinder stroke. An adjustment can be made to compensate for actual conditions during the RVP measurement—sample cylinder at 32° F. to 40° F. and measuring cylinder at 100° F.

Measuring Cylinder—Air Temperature Equilibrium

The normal test cycle is run with the final sample injection disabled by disconnecting the timer contacts associated with the sample cylinder piston, the four-way valve and the measuring cylinder piston. This checks the temperature equilibrium in the measuring cylinder 51 prior to the introduction of the sample. The pressure in the cylinder with valves 62 and 63 closed, should remain at atmospheric ±0.02 psi to the end of the cycle. Two corrections are possible. The purge air can be heated and the time allowed for the air in the cylinder to reach 100° F. can be increased.

Tubing

During the normal measuring cycle, the tubing connecting the two cylinders 28 and 52 is cleared of water by the final air purge. It is full of air at atmospheric pressure before the final injection of sample. When the sample is trapped in the measuring cylinders, the tubing is full of liquid—this volume is accounted for in the above procedures.

While a certain preferred embodiment of the invention has been specifically disclosed, it should be understood that the invention is not limited thereto as many variations will be readily apparent to those skilled in the art and the invention is to be given its broadest possible interpretation within the terms of the following claims.

What is claimed is:

1. An apparatus for determining the Reid Vapor Pressure of normally liquid hydrocarbon materials comprising:
   (a) a first compartment maintained at a substantially fixed temperature in the range of 32° F. to 40° F.,
   (b) a second compartment maintained at a substantially fixed temperature of 100° F.,
   (c) a sample storage container and a sample cylinder within said first compartment, and means connecting said storage container and said sample cylinder for transferring a sample of said liquid hydrocarbon material from said storage container to said sample cylinder,
   (d) a measuring cylinder within said second compartment, and means connecting said measuring cylinder to said sample cylinder in said first compartment for transferring a metered quantity of said sample of said liquid hydrocarbon from said sample cylinder to said measuring cylinder,
   (e) pressure sensor means associated with said measuring cylinder for measuring the pressure within said measuring cylinder,
   (f) and means for displaying said measured pressure as the vapor pressure of said sample of liquid hydrocarbon fuel.

2. The apparatus of claim 1 wherein said first compartment is adapted for receiving and removal of said sample storage container, and said sample storage container has an upright and inverted position, and said first compartment is adapted for positioning said sample storage container in either of said positions.

3. The apparatus of claim 1 wherein said first and second compartments contain substances which remains fluid at temperatures from approximately 32° F. to 100° F. and said sample storage container, said sample cylinder, said measuring cylinder, and said means connecting said container and said cylinders with each other are immersed in said fluids.

4. The apparatus of claim 3 wherein said sample storage container and said sample cylinder within said first compartment are maintained at approximately 32° F. by melting frozen water within said compartment.

5. The apparatus of claim 3 wherein said measuring cylinder is within said second compartment and maintained at approximately 100° F. by a temperature control system including means for circulating the fluid within said compartment.

6. The apparatus of claim 1 with the addition of sequence controller means which controls operation of said sample cylinder, said measuring cylinder and said means for connecting said sample cylinder and said measuring cylinders to transfer said sample to said measuring cylinder for measurement of said pressure therein.

7. The apparatus of claim 6 wherein valve and conduit systems interconnect said sample cylinder and said measuring cylinder and said sequence controller controls operation of said systems.

8. The apparatus of claim 1 with the addition of input air and water systems and means connecting said input systems to said sample cylinder and said measuring cylinder to prepare said cylinders for said measurement of pressure of said sample.

9. The apparatus of claim 8 wherein said means connecting said input systems to said sample cylinder and said measuring cylinder are controlled by a sequence controller to prepare said cylinders for said measurement of vapor pressure of said sample.

10. The apparatus of claim 9 wherein said air and said water input are connected to said cylinders in sequence under control of said sequence controller
 (i) to purge said cylinders and said means connecting said cylinders and
 (ii) to provide water-saturated air in preparation for measurement of pressure of said sample.

11. The apparatus of claim 1 wherein:
(a) said sample storage container is immersed in a fluid in said first compartment,
 said sample cylinder is immersed in a fluid in said first compartment,
 air and water input systems are connected to said sample storage container and said sample cylinder in said first compartment, and means for controlling input from said system including valves for controlling supply of said air and water to said system,
 a four-way valve immersed in said fluid in said first compartment,
 a first means connecting said sample storage container to said sample cylinder through said four-way valve, a second means connecting said sample cylinder to said measuring cylinder through said four-way valve, and a third means for connecting said air and water input supply to said sample cylinder and said measuring cylinder through said four-way valve,
(b) said sample measuring cylinder is immersed in a fluid in said second compartment,
 a first and second valve systems connected to said measuring cylinder at the base thereof,
 said first valve being in said second means connecting said sample cylinder to said measuring cylinder,
 said second valve providing a drain system for said measuring cylinder,
 means within said second compartment for shaking at least said measuring cylinder,
 means within said second compartment for circulating said fluid therein to maintain said entire liquid at substantially said 100° F.,
(c) first operating means operable upon said sample cylinder for
 (i) withdrawing a sample of said liquid hydrocarbon from said sample storage container through said first connecting means and said four-way valve, and
 (ii) for discharging said sample of liquid hydrocarbon through said four-way valve to said measuring cylinder,
(d) second operating means operable upon said measuring cylinder for drawing materials through said first valve including separately air, water of said sample of liquid hydrocarbon from said sample cylinder,
 said air and water functioning to clean and purge said sample system and said drawn sample of liquid hydrocarbon being a measured quantity of said liquid hydrocarbon whose vapor pressure is to be determined,
(e) a sequence controller for operating said four-way valve, said first and second valve systems, said first and second operating means, and said air and water input system to draw said sample of liquid hydrocarbon into said measuring cylinder, said sequence controller further including means for closing said first and second valve systems and for expanding the volume within said measuring cylinder containing said sample of liquid hydrocarbon,
(f) and means for measuring within said measuring cylinder the pressure of the vapor phase of said sample of liquid hydrocarbon.

12. The apparatus of claim 11 including means for maintaining said fluid within said first compartment at a substantially fixed temperature in the range of 32° F. to 40° F. comprising a source for cooling said fluid.

13. The apparatus of claim 11 wherein said source is melting frozen water.

14. The apparatus of claim 11 including means for maintaining said fluid within said second compartment at a substantially fixed temperature in the range of 100° F.±0.2° F. comprising a source for heating said fluid.

15. A method for measuring Reid Vapor Pressure of a liquid hydrocarbon comprising the steps of:
(a) filling a sample container with a known volume of said liquid hydrocarbon at a temperature within the range of 32° F. to 40° F.
(b) preparing a measuring container having an initial volume at 100° F. and atmospheric pressure, equal to four times the volume of said liquid hydrocarbon in said first container,
(c) tightly coupling said two containers,
(d) sealing said measuring container,
(e) transferring said liquid hydrocarbon from said first container into said measuring container, and expanding said measuring container by the volume of said first container.
(f) and measuring the vapor pressure in said second container after equilibration as said desired Reid Vapor Pressure.

16. The method of claim 15 wherein said containers are cylinders and said transfer of said liquid and expansion of said measuring container is effected by moving fluid-tight pistons within said cylinders.

17. The method of claim 15 wherein said measuring container is shaken after said measuring container has been expanded and after said liquid hydrocarbon has been transferred thereto to effect said equilibration.

18. The method of claim 15 wherein said measuring container is prepared with water saturated air at 100° F. and atmospheric pressure.

19. The method of claim 15 wherein the preparation and expansion of said measuring container is compensated for the volume of the coupling conduits between said sample and said measuring container whereby said expanded measuring container maintains said volume equal to four times said sample volume.

20. The method of claim 15 wherein said sample container is continuously maintained at said 32° F. to 40° F. and said measuring container is continuously maintained at said 100° F. at atmospheric pressure until said sample is transferred to said measuring container, and said containers are tightly coupled during said filling, expanding and measuring steps.

* * * * *